US012285218B2

(12) United States Patent
He (10) Patent No.: US 12,285,218 B2
(45) Date of Patent: Apr. 29, 2025

(54) SUBJECTIVE AND OBJECTIVE INTEGRATED PRECISE OPTOMETRY DEVICE, AND OPTOMETRY METHOD

(71) Applicant: Zhejiang Aizhitong Medical Technology Co., Ltd., Zhejiang (CN)

(72) Inventor: Liangyi He, Beijing (CN)

(73) Assignee: Zhejiang Aizhitong Medical Technology Co., Ltd., Zhejiang (CN)

( * ) Notice: Subject to any disclaimer, the term of this patent is extended or adjusted under 35 U.S.C. 154(b) by 509 days.

(21) Appl. No.: 17/753,157

(22) PCT Filed: Feb. 18, 2020

(86) PCT No.: PCT/CN2020/075652
§ 371 (c)(1),
(2) Date: Feb. 22, 2022

(87) PCT Pub. No.: WO2021/031538
PCT Pub. Date: Feb. 25, 2021

(65) Prior Publication Data
US 2022/0330820 A1    Oct. 20, 2022

(30) Foreign Application Priority Data

Aug. 22, 2019  (CN) .......................... 201910777661.8
Aug. 22, 2019  (CN) .......................... 201910777914.1

(51) Int. Cl.
*A61B 3/18* (2006.01)
*A61B 3/00* (2006.01)
(Continued)

(52) U.S. Cl.
CPC .............. *A61B 3/18* (2013.01); *A61B 3/0083* (2013.01); *A61B 3/0091* (2013.01); *A61B 3/028* (2013.01);
(Continued)

(58) Field of Classification Search
CPC ....... A61B 3/18; A61B 3/0083; A61B 3/0091; A61B 3/028; A61B 3/1015; A61B 3/12;
(Continued)

(56) References Cited

U.S. PATENT DOCUMENTS

2007/0115431 A1* 5/2007 Smith, III ................. A61F 2/16
                                                      351/221
2012/0162606 A1* 6/2012 Nakamura ............. A61B 3/032
                                                      351/221
(Continued)

FOREIGN PATENT DOCUMENTS

CN          1194131 A        9/1998
CN        102188231 A        9/2011
(Continued)

OTHER PUBLICATIONS

Brien A. Holden et al., "Global Prevalence of Myopia and High Myopia and Temporal Trends from 2000 through 2050"; American Academy of Ophthalmology; May 2016 (Available online Feb. 1, 2016); vol. 123, No. 5; pp. 1036-1042.

*Primary Examiner* — Mohammed A Hasan
(74) *Attorney, Agent, or Firm* — NKL Law; Allen Xue (57) ABSTRACT

A subjective and objective integrated precise optometry device, and an optometry method are provided. The device has a left eye optical path and a right eye optical path. Each of the single eye optical paths comprises a human eye refraction objective measurement subsystem, a human eye refraction correction subsystem, an eyeball positioning subsystem, and a subjective visual function testing subsystem. The device has functions such as objective measurement for monocular and binocular refraction, continuous subjective optometry, interpupillary distance measurement, and monocular and binocular visual function measurement (comprising, but not limited to, vision and stereopsis), and can implement subjective and objective integrated precise mon-
(Continued)

ocular and binocular optometry. Additionally, the device has such functions as rapid measurement and screening of human eye refraction, and preliminary screening of human eye diseases (except for ametropia), and can be used for optometry, ophthalmological clinical triage, population ametropia screening and monitoring, etc.

9 Claims, 4 Drawing Sheets

(51) Int. Cl.
  *A61B 3/028* (2006.01)
  *A61B 3/10* (2006.01)
  *A61B 3/12* (2006.01)
  *A61B 3/14* (2006.01)

(52) U.S. Cl.
  CPC .............. *A61B 3/1015* (2013.01); *A61B 3/12* (2013.01); *A61B 3/14* (2013.01)

(58) Field of Classification Search
  CPC ........... A61B 3/14; A61B 3/032; A61B 3/103; A61B 3/1035
  USPC ........................................................ 351/206
  See application file for complete search history.

(56) References Cited

U.S. PATENT DOCUMENTS

| | | | |
|---|---|---|---|
| 2014/0313485 A1* | 10/2014 | Umekawa | A61B 3/152 351/246 |
| 2015/0374233 A1 | 12/2015 | Zhang et al. | |
| 2016/0095512 A1* | 4/2016 | Shimizu | A61B 3/103 351/205 |
| 2016/0345824 A1 | 12/2016 | Sakurada | |
| 2017/0135572 A1 | 5/2017 | Takii et al. | |
| 2017/0325682 A1 | 11/2017 | Liang | |
| 2020/0245860 A1* | 8/2020 | Umano | A61B 3/0016 |

FOREIGN PATENT DOCUMENTS

| | | |
|---|---|---|
| CN | 102307514 A | 1/2012 |
| CN | 102525399 A | 7/2012 |
| CN | 105105707 A | 12/2015 |
| CN | 206273246 U | 6/2017 |
| CN | 106963335 A | 7/2017 |
| CN | 107890335 A | 4/2018 |
| CN | 109561823 A | 4/2019 |
| CN | 109770844 A | 5/2019 |
| CN | 109893081 A | 6/2019 |
| CN | 110367924 A | 10/2019 |
| CN | 110367925 A | 10/2019 |
| JP | 2018143554 A | 9/2018 |
| JP | 2018143571 A | 9/2018 |
| WO | 2017218539 A1 | 12/2017 |

* cited by examiner

SUBJECTIVE AND OBJECTIVE INTEGRATED PRECISE OPTOMETRY DEVICE, AND OPTOMETRY METHOD

TECHNICAL FIELD

The present invention relates to the technical field of optical measurement, in particular to a subjective and objective integrated precise optometry device, and an optometry method.

BACKGROUND

There are two most important causes for visual impairment caused by uncorrected ametropia (including myopia, hyperopia and astigmatism) and surgically untreated cataract (see Document [J]. Ophthalmology 2016; 123(5):1036-1042). It is critical for patent's refraction correction to accurately measure the degree of human eye ametropia and determine the best correction prescription.

Currently, the optometry process consists of two steps: objective optometry and subjective optometry. The objective optometry method includes retinoscopy optometry and objective measurement for the patient's ametropia by virtue of professional equipment such as auto-refractor and human eye aberrometer. On this basis, the subjective optometry is then performed using a trial frame insert or a phoropter. Since the objective optometry does not include subjective feedback from a subject, its detection results are usually for reference only. However, the accuracy and repeatability of the subjective optometry is dependent on the degree of cooperation of the person under examination, the level and clinical experience of the examiner to a great degree, making the quality of correction prescriptions obtained on the basis of the existing subjective optometry methods vary. More importantly, the existing trial frame insert or the phoropter is used for subjective optometry by virtue of a trial lens at a discrete degrees (step size: 0.25 D), which has rounding errors and cannot achieve the continuous precise optometry for the human eye ametropia.

In 2018, a study made by the World Health Organization reported that there were 600 million myopes in China, and the myopia rate among teenagers has already been the highest in the world, and still on the rise. According to the current development trend of the myopia, most teenagers, who suffer from the early onset myopia, must be detected early and treated promptly, so that it is very important for the children to screen vision and monitor refractive data from their childhood. If you see a doctor for eye discomfort, the clinician will make a diagnosis upon examination. One of the main symptoms of eye diseases is vision loss, so that the optic examination is a routine clinical examination in ophthalmology. At present, the result of whether the vision is normal can be given only due to the fact that the vision is clinically examined by the visual chart, and thus the vision loss cannot be determined to be caused by the ametropia or other eye diseases, which does not facilitate the ophthalmological clinical triage.

Regarding the current separating subjective and objective optometry methods (by different kinds of equipment), the rounding errors of the subjective optometry caused by the great influence from human factors and discontinuous degrees of trial lenses, and requirements for rapid vision screening, ametropia monitoring and clinical vision screening & triage in ophthalmology among juvenile myopia group, the present invention provides a subjective and objective integrated precise optometry device, and an optometry method, which are capable of simultaneously conducting binocular refraction measurement, continuous subjective optometry, interpupillary distance measurement, and visual function measurement (comprising, but not limited to, vision and stereopsis), and realizing the binocular subjective and objective integrated precise optometry; and meanwhile, of rapidly screening the human eye ametropia and preliminarily screening whether the human eyes suffer from diseases (excluding ametropia), thus being used for screening of human eye ametropia, refraction data monitoring and ophthalmological clinical triage.

SUMMARY OF THE INVENTION

The technical problems are solved by the present invention is to: provide a subjective and objective integrated precise optometry device, and an optometry method for solving the current separating subjective and objective optometry methods (by different kinds of equipment), large human factor of subjective optometry, rounding error due to discontinuity of test lenses and meeting the requirements for rapid population ametropia screening, ametropia monitoring and ophthalmological clinical triage for the ametropia group, which is capable of simultaneously conducting objective binocular refraction measurement, continuous subjective optometry, interpupillary distance measurement, and visual function measurement (comprising, but not limited to, vision and stereopsis), realizing the binocular subjective and objective integrated precise optometry; and meanwhile, of rapidly screening the human eye ametropia and preliminarily screening whether the human eyes suffer from diseases (excluding ametropia), thus being used for optometry, screening of human eye ametropia, refraction data monitoring and ophthalmological clinical triage.

For this, the present invention first provides a subjective and objective integrated precise optometry device, the device comprising a left eye optical path and a right eye optical path; each of single eye optical paths comprises an objective human eye refraction measurement subsystem, a human eye refraction correction subsystem, an eyeball positioning subsystem and a subjective visual function test subsystem, wherein the objective human eye refraction measurement subsystem is used for objective measurement of human eye refraction; the human eye refraction correction subsystem is used for correction of human eye defocus and astigmatism; the eyeball positioning subsystem is used for eyeball positioning; and the subjective visual function test subsystem is used for visual function test at the time of subjective optometry.

Preferably, each of single eye optical paths further comprises a visual function diagnosis subsystem, which is used for collecting subjective test information of a person under examination and giving a diagnosis result.

Further preferably, the objective human eye refraction measurement subsystem may be selected from a wavefront measurement technology, a retinoscopy optometry technology, a grating focused optometry, a Scheiner plate optometry technology and a blade measurement optometry technology.

Further preferably, the wavefront measurement technology may be selected from a Hartmann wavefront sensor based on microlens array, a Hartmann wavefront sensor based on microprism array, a curvature wavefront sensor and a pyramid wavefront sensor.

Further preferably, the objective human eye refraction measurement subsystem comprises a near-infrared beacon light source (9), a collimating objective (10), a reflector (12), a second spectroscope (13), a first spectroscope (5), a first relay telescope (3), a second relay telescope (6) and a wavefront sensor (7); the human eye refraction correction subsystem comprises a first relay telescope (3) and a cylindrical lens pair (4); the eyeball positioning subsystem comprises a pupil imaging device (2); and the subjective visual function test subsystem comprises a visual target display device (8) and a visual target objective (11); a cylindrical lens pair (4) is provided at a conjugate place of a pupil of a human eye (1), a light emitted by a near-infrared beacon light source (9) is collimated by the collimating objective (10), and then reflected by the second spectroscope (13) and the first spectroscope (5), and finally enters the human eye (1) through the cylindrical lens pair (4), the first relay telescope (3) and the pupil imaging device (2); the light reflected from the fundus of the human eye (1) enters the wavefront sensor (7) through the pupil imaging device (2), the first relay telescope (3), the cylindrical lens pair (4), the first spectroscope (5) and the second relay telescope (6), so as to objectively measure the refractive error of the human eye; and according to the measured refractive error of the human eye, a distance between the two lenses of the first relay telescope (3) along an optical axis is changed to compensate for the human eye defocus, and the cylindrical lens pair (4) is revolved around the optical axis to compensate for the human eye astigmatism; upon the compensation for the refractive error of the human eye, the visual target display device (8) displays a specific visual target, the human eye (1) observes the visual target displayed on the visual target display device (8) through the first relay telescope (3), the cylindrical lens pair (4), the first spectroscope (5), the second spectroscope (13), the reflector (12) and the visual target lens (11).

Further preferably, the cylindrical lens pair (4) may be selected from a plano-concave/plano-convex cylindrical lens pair, a plano-concave/plano-concave cylindrical lens pair and a plano-convex/plano-convex cylindrical lens pair of the same or different focal power.

Further preferably, the visual target display device (8) may be selected from a CRT display, a commercial projector, a liquid crystal display, a plasma display, an electroluminescent display, an organic light emitting display, a projection display device and a printed visual chart.

Further preferably, an internal focusing device (30) is used for replacing the first relay telescope (3), and comprises a first reflector (14), a first lens (15), a second reflector (16), a third reflector (17), a second lens (18) and a fourth reflector (19).

The present invention further provides an optometry method based on the foregoing subjective and objective integrated precise optometry device, the method comprising the following steps that:

S1. a near-infrared beacon light source (9) is started to give out light, which is collimated by a collimating objective (10), and then reflected by a second spectroscope (13) and a first spectroscope (5), and finally enters a human eye (1) through a cylindrical lens pair (4) and a first relay telescope (3);

S2. the light reflected from the fundus of the human eye (1) enters the wavefront sensor (7) through the pupil imaging device (2), the first relay telescope (3), the cylindrical lens pair (4), the first spectroscope (5) and the second relay telescope (6), so as to objectively measure the refractive error of the human eye;

S3. according to the measured refractive error of the human eye, a distance between the two lenses of the first relay telescope (3) along an optical axis is changed to compensate for the human eye defocus based on a human eye defocus correction formula; and according to the measured refractive error of the human eye, a single cylindrical lens in the cylindrical lens pair (4) is respectively revolved around an optical axis to compensate for the human eye astigmatism based on a human eye astigmatism correction formula;

S4. upon the compensation for the refractive error of the human eye, the visual target display device (8) displays a specific visual target, the human eye observes and judges the specific visual target displayed on the visual target display device (8) through the first relay telescope (3), the cylindrical lens pair (4), the first spectroscope (5), the second spectroscope (13), the reflector (12) and the visual target lens (11);

S5. the defocus is slightly adjusted according to the subjective visual perception, the relative angle of the cylindrical lens pair 4 is rotated to slightly adjust and synthesize the magnitude and axial direction of astigmatism till the subjective optimal visual correction quality is obtained, thus finishing the subjective optometry for the single eye;

S6. upon the subjective optometry for the left and right eyes, a left optical path and a right optical path are integrally moved in a vertical direction of optical axis to adjust the pupil distance for red & green and binocular adjustment process, so as to finally give out the best precise binocular refraction correction prescription.

The present invention further provides an optometry method based on the foregoing subjective and objective integrated precise optometry device, the method comprising the following steps that:

S1. a near-infrared beacon light source (9) is started to give out light, which is collimated by a collimating objective (10), and then reflected by a second spectroscope (13) and a first spectroscope (5), and finally enters a human eye (1) through a cylindrical lens pair (4) and a first relay telescope (3);

S2. the light reflected from the fundus of the human eye (1) enters the wavefront sensor (7) through the pupil imaging device (2), the first relay telescope (3), the cylindrical lens pair (4), the first spectroscope (5) and the second relay telescope (6), so as to objectively measure the refractive error of the human eye;

S3. according to the measured refractive error of the human eye, a distance between the two lenses of the first relay telescope (3) along an optical axis is changed to compensate for the human eye defocus based on a human eye defocus correction formula; and according to the measured refractive error of the human eye, a single cylindrical lens in the cylindrical lens pair (4) is respectively revolved around an optical axis to compensate for the human eye astigmatism based on a human eye astigmatism correction formula;

S4. upon the compensation for the refractive error of the human eye, the visual target display device (8) displays a specific visual target, the human eye observes and judges the specific visual target displayed on the visual target display device (8) through the first relay telescope (3), the cylindrical lens pair (4), the first spectroscope (5), the second spectroscope (13), the reflector (12) and the visual target lens (11);

S5. a visual function diagnosis subsystem makes a diagnosis according to the judgment of a person under examination, and an eye under examination is only believed to suffer from ametropia and an ametropia measurement value is given if the person under examination makes a correct judgment; and if the person under examination misjudges, it is believed that the eye under examination may have other eye diseases except the ametropia, and thus needs to be confirmed with other eye examinations.

Compared with the prior art, the present invention has the following advantages: The present invention first provides the subjective and objective integrated precise optometry device, and the optometry method, wherein the objective dioptometry technology is applied for objective measurement on the human eye diopter, so as to guide the first relay telescope and the rotary cylindrical lens pair to compensate for the human eye defocus and astigmatism; by virtue of observing the built-in visual target, the person under examination slightly adjusts the defocus amount, magnitude and axial direction of astigmatism according to the subjective visual perception so as to realize the precise subjective optometry, conducts red & green and binocular balance adjustment process on this basis, and finally gives the optimal precise refraction correction prescription; and meanwhile, the present invention has such functions as rapid screening of the human eye ametropia and preliminarily screening whether the human eyes suffer from diseases (excluding ametropia), thus being used for optometry, population ametropia screening and monitoring, and ophthalmological clinical triage.

DETAILED DESCRIPTION OF THE PREFERRED EMBODIMENTS

The present invention will be further illustrated in combination with specific embodiments and drawings. It should be emphasized that the following description is only illustrative, but is not intended to limit the scope and application of the present invention. Besides, the description of well-known structure and technology is omitted in the following paragraphs, so as to prevent the concept of the present invention from being confused unnecessarily.

The present invention provides a subjective and objective integrated precise optometry device, the device comprising a left eye optical path and a right eye optical path; each of single eye optical paths comprises an objective human eye refraction measurement subsystem, a human eye refraction correction subsystem, an eyeball positioning subsystem and a subjective visual function test subsystem, wherein the objective human eye refraction measurement subsystem is used for objective measurement of human eye refraction; the human eye refraction correction subsystem is used for correction of human eye defocus and astigmatism; the eyeball positioning subsystem is used for eyeball positioning; and the subjective visual function test subsystem is used for visual function test at the time of subjective optometry.

The objective human eye refraction measurement subsystem may be realized by selecting a wavefront measurement technology, a retinoscopy optometry technology, a grating focused optometry, a Scheiner plate optometry technology and a blade measurement optometry technology, and the present invention preferably selects the wavefront measurement technology. The wavefront measurement technology may be selected from a Hartmann wavefront sensor based on microlens array, a Hartmann wavefront sensor based on microprism array, a curvature wavefront sensor and a pyramid wavefront sensor.

The subjective and objective integrated precise optometry device according to the present invention will be elaborated by virtue of different embodiments in the following paragraphs.

Embodiment 1

Figure 1:
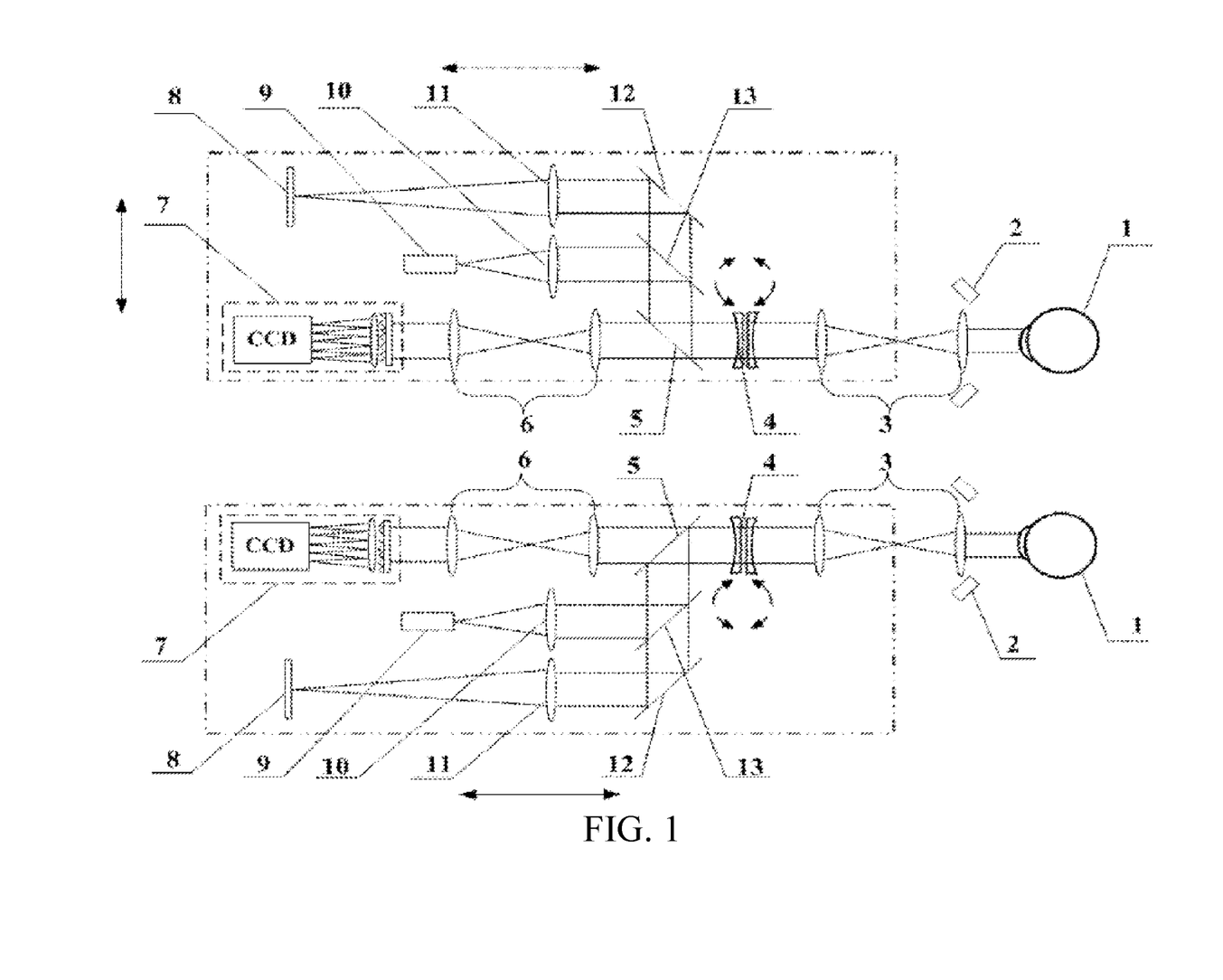
FIG. 1 is a schematic diagram of Embodiment 1 of a subjective and objective integrated precise optometry device according to the present invention.

As shown in FIG. 1, the objective human eye refraction measurement subsystem comprises a near-infrared beacon light source 9, a collimating objective 10, a reflector 12, a second spectroscope 13, a first spectroscope 5, a first relay telescope 3, a second relay telescope 6 and a wavefront sensor 7; the human eye refraction correction subsystem comprises a first relay telescope 3 and a cylindrical lens pair 4; the eyeball positioning subsystem comprises a pupil imaging device 2; and the subjective visual function test subsystem comprises a visual target display device 8 and a visual target objective 11. It should be noted that the objective human eye refraction measurement subsystem and the human eye refraction correction subsystem share the first relay telescope 3.

The cylindrical lens pair 4 is provided at a conjugate place of a pupil of a human eye 1, a light emitted by a near-infrared beacon light source 9 is collimated by the collimating objective 10, and then reflected by the second spectroscope 13 and the first spectroscope 5, and finally enters the human eye 1 through the cylindrical lens pair 4, the first relay telescope 3 and the pupil imaging device 2; the light reflected from the fundus of the human eye 1 enters the wavefront sensor 7 through the pupil imaging device 2, the first relay telescope 3, the cylindrical lens pair 4, the first spectroscope 5 and the second relay telescope 6, so as to objectively measure the refractive error of the human eye (defocus, astigmatism and astigmatism axial direction); and according to the measured refractive error of the human eye, a distance between the two lenses of the first relay telescope 3 along an optical axis is changed to compensate for the human eye defocus, and the cylindrical lens pair 4 is revolved around the optical axis to compensate for the human eye astigmatism; upon the compensation for the refractive error of the human eye, the visual target display device 8 displays a specific visual target, the human eye 1 observes the visual target displayed on the visual target display device 8 through the first relay telescope 3, the cylindrical lens pair 4, the first spectroscope 5, the second spectroscope 13, the reflector 12 and the visual target lens 11.

In the embodiment, the cylindrical lens pair 4 may be selected from a plano-concave/plano-convex cylindrical lens pair, a plano-concave/plano-concave cylindrical lens pair and a plano-convex/plano-convex cylindrical lens pair of the same or different focal power. The visual target display device 8 may be selected from a CRT display, a commercial projector, a liquid crystal display, a plasma display, an electroluminescent display, an organic light emitting display, a projection display device and a printed visual chart.

Based on the subjective and objective integrated precise optometry device of the embodiment, the present invention further provides an optometry method, the method comprising the following steps:

S1. a near-infrared beacon light source 9 is started to give out light, which is collimated by a collimating objective 10, and then reflected by a second spectroscope 13 and a first spectroscope 5, and finally enters a human eye 1 through a cylindrical lens pair 4 and a first relay telescope 3;

S2. the light reflected from the fundus of the human eye 1 enters the wavefront sensor 7 through the pupil imaging device 2, the first relay telescope 3, the cylindrical lens pair 4, the first spectroscope 5 and the second relay telescope 6, so as to objectively measure the refractive error of the human eye;

S3. according to the measured refractive error of the human eye, a distance between the two lenses of the first relay telescope 3 along an optical axis is changed to compensate for the human eye defocus based on a human eye defocus correction formula; and according to the measured refractive error of the human eye, a single cylindrical lens in the cylindrical lens pair 4 is respectively revolved around an optical axis to compensate for the human eye astigmatism based on a human eye astigmatism correction formula;

S4. upon the compensation for the refractive error of the human eye, the visual target display device 8 displays a specific visual target, the human eye observes and judges the specific visual target displayed on the visual target display device 8 through the first relay telescope 3, the cylindrical lens pair 4, the first spectroscope 5, the second spectroscope 13, the reflector 12 and the visual target lens 11;

S5. the defocus is slightly adjusted according to the subjective visual perception, the relative angle of the cylindrical lens pair 4 is rotated to slightly adjust and synthesize the magnitude and axial direction of astigmatism till the subjective optimal visual correction quality is obtained, thus finishing the subjective optometry for the single eye;

S6. upon the subjective optometry for the left and right eyes, a left optical path and a right optical path are integrally moved in a vertical direction of optical axis to adjust the pupil distance for red & green and binocular adjustment process, so as to finally give out the best precise binocular refraction correction prescription.

The compensation for defocus is conducted by integrally moving the double dotted box in FIG. 1 for internal focusing.

In the embodiment, the human eye defocus correction formula is as follows:

$$D = [d-(f_1+f_2)]\Phi \quad (1)$$

where, D is a corrective defocus, $f_1$ and $f_2$ are focal lengths of the two lenses in the first relay telescope 3, d is a distance between the two lenses in the first relay telescope 3 in a direction of optical axis, and Φ is determined by the focal lengths of the two lenses in the first relay telescope 3. As can be seen from Formula 1, the human eye defocus may be continuously corrected by virtue of changing the distance between the two lenses in the first relay telescope 3 in a direction of optical axis.

The human eye astigmatism correction formula is as follows:

$$C = 2F_c \cos(a_1 - a_2) \quad (2)$$

$$\phi = \left(\frac{a_1 + a_2}{2}\right)$$

where, C and Φ are corrective magnitude and axial direction of astigmatism respectively, $F_c$ is magnitude of astigmatism of the single cylindrical lens in the cylindrical lens pair 4, and $a_1$ and $a_2$ are axial directions of astigmatism of two cylindrical lenses. As can be seen from Formula (2), the human eye astigmatism may be continuously corrected by virtue of revolving the single cylindrical lens in the cylindrical lens pair 4 respectively.

Embodiment 2

Figure 2:
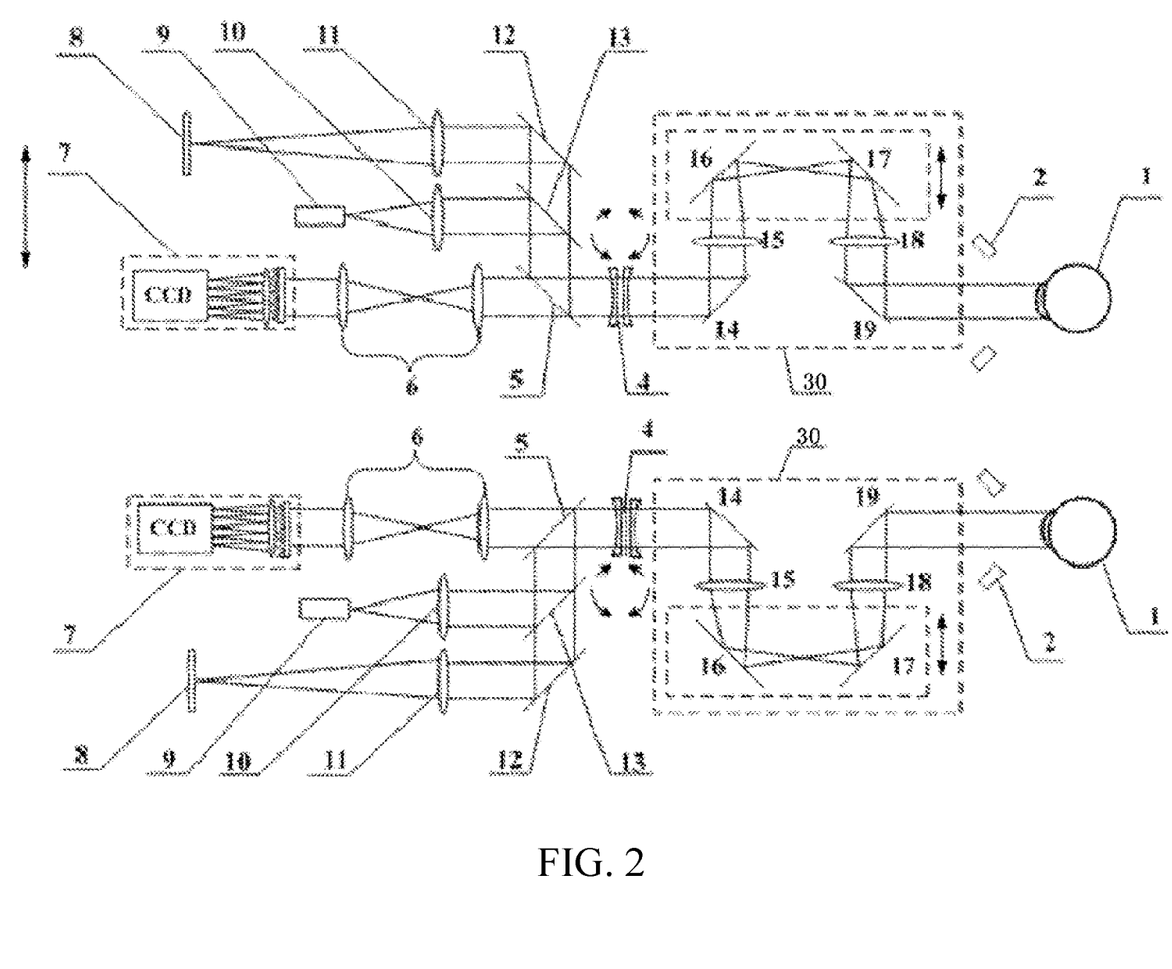
FIG. 2 is a schematic diagram of Embodiment 2 of a subjective and objective integrated precise optometry device according to the present invention.

As shown in FIG. 2, the subjective and objective integrated precise optometry device of the embodiment is structurally the same as Embodiment 1, but the differences therebetween lie in that an internal focusing device 30 is used for replacing the first relay telescope 3, and comprises a first reflector 14, a first lens 15, a second reflector 16, a third reflector 17, a second lens 18 and a fourth reflector 19, and a structure thereof is shown by a dashed box in FIG. 2.

Meanwhile, the present invention also sets forth an optometry method which is the same as the one in Embodiment 1.

The human eye astigmatism correction methods are the same in Embodiment 2 and Embodiment 1. The correction of human eye defocus differs from the one in Embodiment 1 in that $f_1$, $f_2$ and d in Formula (1) are the focal lengths of the first lens 15 and the second lens 18 respectively as well as the distance therebetween, and the second reflector 16 and the third reflector 17 are integrally moved to change the distance between the first lens 15 and the second lens 18 in the direction of optical axis to compensate for the human eye defocus.

Embodiment 3

Figure 3:
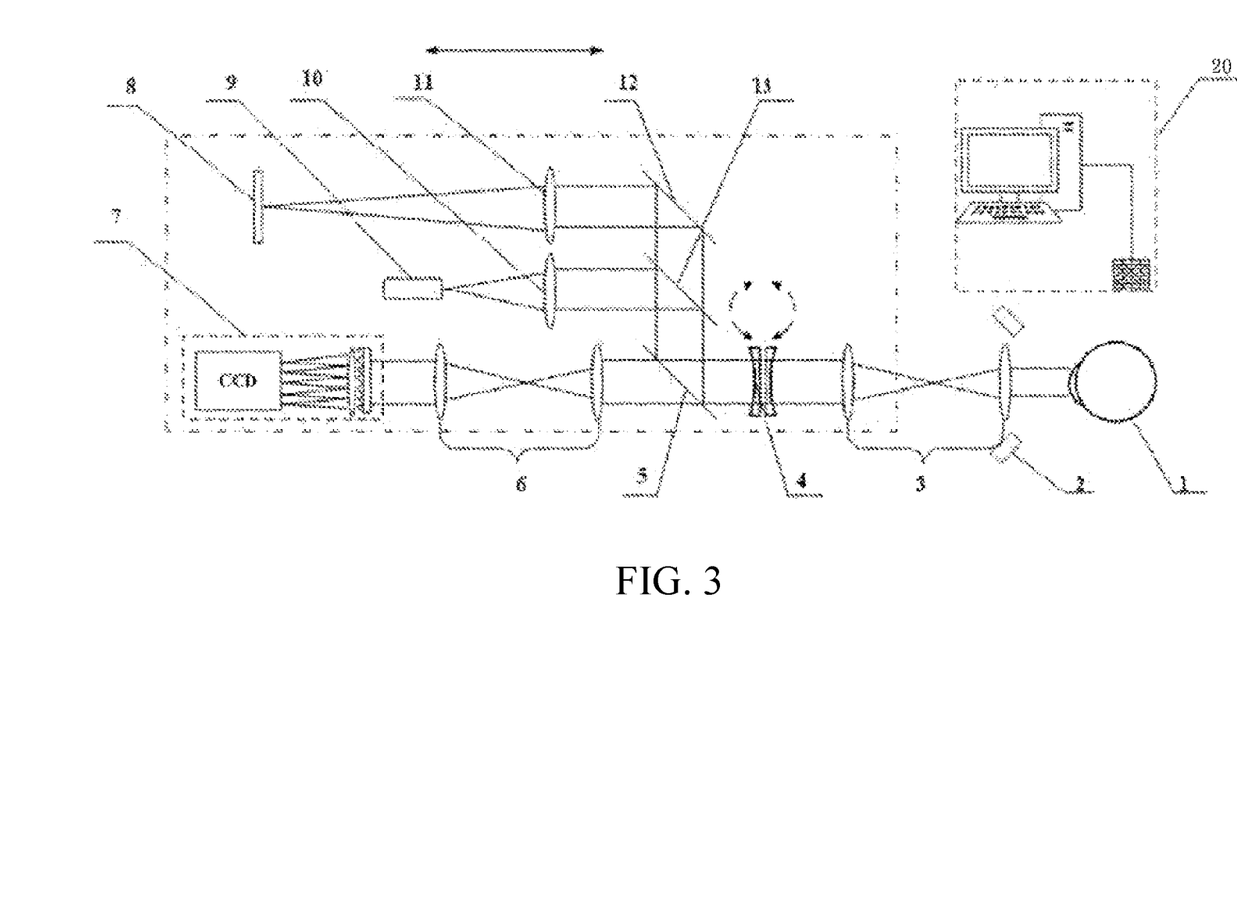
FIG. 3 is a schematic diagram of Embodiment 3 of a subjective and objective integrated precise optometry device according to the present invention.

As shown in FIG. 3, the subjective and objective integrated precise optometry device in the embodiment is structurally the same as the one in Embodiment 1, and the differences therebetween lie in that each of single eye optical paths in the embodiment further comprises a visual function diagnosis subsystem 20, which is used for collecting subjective test information of a person under examination and giving a diagnosis result.

Meanwhile, the present invention also sets forth an optometry method, the method comprising the following steps:

S1. a near-infrared beacon light source 9 is started to give out light, which is collimated by a collimating objective 10, and then reflected by a second spectroscope 13 and a first spectroscope 5, and finally enters a human eye 1 through a cylindrical lens pair 4 and a first relay telescope 3;

S2. the light reflected from the fundus of the human eye 1 enters the wavefront sensor 7 through the pupil imaging device 2, the first relay telescope 3, the cylindrical lens pair 4, the first spectroscope 5 and the second relay telescope 6, so as to objectively measure the refractive error of the human eye;

S3. according to the measured refractive error of the human eye, a distance between the two lenses of the first relay telescope 3 along an optical axis is changed to compensate for the human eye defocus based on a human eye defocus correction formula; and according to the measured refractive error of the human eye, a single cylindrical lens in the cylindrical lens pair 4 is respectively revolved around an optical axis to compensate for the human eye astigmatism based on a human eye astigmatism correction formula;

S4. upon the compensation for the refractive error of the human eye, the visual target display device 8 displays a specific visual target, the human eye observes and judges the specific visual target displayed on the visual target display device 8 through the first relay telescope 3, the cylindrical lens pair 4, the first spectroscope 5, the second spectroscope 13, the reflector 12 and the visual target lens 11;

S5. a visual function diagnosis subsystem 20 makes a diagnosis according to the judgment of a person under examination, and an eye under examination is only believed to suffer from ametropia and an ametropia measurement value is given if the person under examination makes a correct judgment; and if the person under examination misjudges, it is believed that the eye under examination may have other eye diseases except the ametropia, and thus needs to be confirmed with other eye examinations (for example, fundus photography).

Embodiment 4

Figure 4:
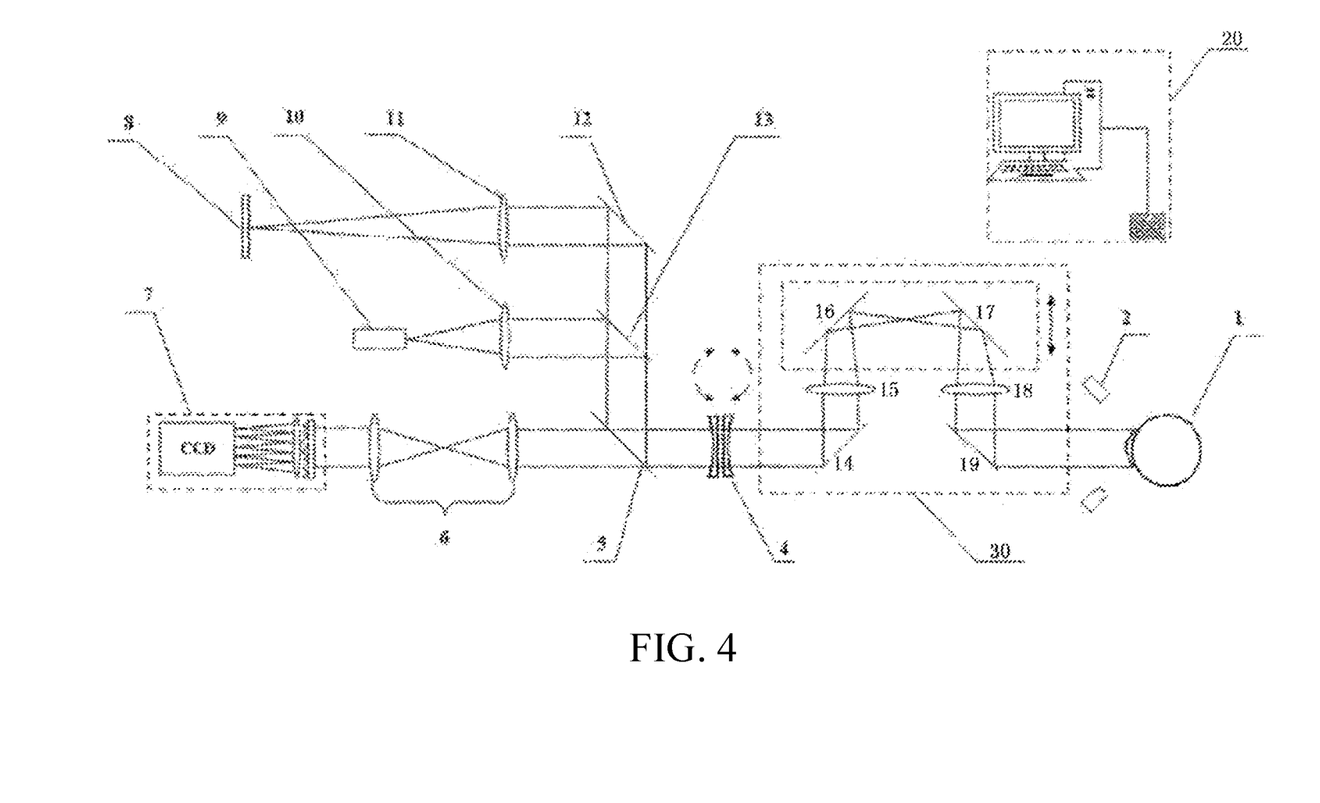
FIG. 4 is a schematic diagram of Embodiment 4 of a subjective and objective integrated precise optometry device according to the present invention.

As shown in FIG. 4, the subjective and objective integrated precise optometry device in the embodiment is structurally the same as the one in Embodiment 2, and the differences therebetween lie in that each of single eye optical paths in the embodiment further comprises a visual function diagnosis subsystem 20, which is used for collecting subjective test information of a person under examination and giving a diagnosis result.

Meanwhile, the present invention also sets forth an optometry method, the method comprising the following steps:

S1. a near-infrared beacon light source 9 is started to give out light, which is collimated by a collimating objective 10, and then reflected by a second spectroscope 13 and a first spectroscope 5, and finally enters a human eye 1 through a cylindrical lens pair 4 and a first relay telescope 3;

S2. the light reflected from the fundus of the human eye 1 enters the wavefront sensor 7 through the pupil imaging device 2, the first relay telescope 3, the cylindrical lens pair 4, the first spectroscope 5 and the second relay telescope 6, so as to objectively measure the refractive error of the human eye;

S3. according to the measured refractive error of the human eye, the second reflector 16 and the third reflector 17 are integrally moved to change the distance between the first lens 15 and the second lens 18 in the direction of optical axis to compensate for the human eye defocus. according to the measured refractive error of the human eye, a single cylindrical lens in the cylindrical lens pair 4 is respectively revolved around an optical axis to compensate for the human eye astigmatism based on a human eye astigmatism correction formula;

S4. upon the compensation for the refractive error of the human eye, the visual target display device 8 displays a specific visual target, the human eye observes and judges the specific visual target displayed on the visual target display device 8 through the first relay telescope 3, the cylindrical lens pair 4, the first spectroscope 5, the second spectroscope 13, the reflector 12 and the visual target lens 11;

S5. a visual function diagnosis subsystem 20 makes a diagnosis according to the judgment of a person under examination, and an eye under examination is only believed to suffer from ametropia and an ametropia measurement value is given if the person under examination makes a correct judgment; and if the person under examination misjudges, it is believed that the eye under examination may have other eye diseases except the ametropia, and thus needs to be confirmed with other eye examinations (for example, fundus photography).

So far, the present invention has been described in combination with the preferred embodiments. It will be appreciated by those skilled in the art that other various changes, substitutions and additions are also possible without departing from the spirit and scope of the present invention. Accordingly, the scope of the present invention is not limited to the foregoing specific embodiments, and should be defined by the appended claims.

The invention claimed is:

1. A subjective and objective integrated precise optometry device, comprising:
   a left eye optical path and a right eye optical path, each comprising an objective human eye refraction measurement subsystem, a human eye refraction correction subsystem, an eyeball positioning subsystem, and a subjective visual function test subsystem,
   wherein the objective human eye refraction measurement subsystem comprises a near-infrared beacon light source, a collimating objective, a reflector, a second spectroscope, a first spectroscope, a first relay telescope, a second relay telescope, and a wavefront sensor,
   wherein the human eye refraction correction subsystem comprises a first relay telescope and a cylindrical lens pair,
   wherein the eyeball positioning subsystem comprises a pupil imaging device,
   wherein the subjective visual function test subsystem comprises a visual target display device and a visual target objective,
   wherein a cylindrical lens pair is provided at a conjugate place of a pupil of a human eye, during operation, a light emitted by the near-infrared beacon light source is collimated by the collimating objective, is reflected by the second spectroscope and the first spectroscope, and enters the human eye through the cylindrical lens pair, the first relay telescope, and the pupil imaging device,
   wherein the light reflected from the fundus of the human eye enters the wavefront sensor through the pupil imaging device, the first relay telescope, the cylindrical lens pair, the first spectroscope, and the second relay telescope to objectively measure the refractive error of the human eye,
   wherein, according to the measured refractive error of the human eye, a distance between the two lenses of the first relay telescope along an optical axis is changed to compensate for the human eye defocus, and the cylindrical lens pair is revolved around the optical axis to compensate for the human eye astigmatism; upon the compensation for the refractive error of the human eye, the visual target display device displays a specific visual target, the human eye observes the visual target displayed on the visual target display device through the first relay telescope, the cylindrical lens pair, the first spectroscope, the second spectroscope, the reflector, and the visual target lens.

2. The subjective and objective integrated precise optometry device according to claim 1, wherein each of single eye optical path further comprises a visual function diagnosis subsystem for collecting subjective test information of a person under examination and providing a diagnosis result.

3. The subjective and objective integrated precise optometry device according to claim 1, wherein the objective human eye refraction measurement subsystem is realized by a wavefront measurement technology, a retinoscopy optometry technology, a grating focused optometry technology, a Scheiner plate optometry technology, or a blade measurement optometry technology.

4. The subjective and objective integrated precise optometry device according to claim 3, wherein the wavefront measurement technology is selected from a Hartmann wavefront sensor based on microlens array, a Hartmann wavefront sensor based on microprism array, a curvature wavefront sensor and pyramid wavefront sensor.

5. The subjective and objective integrated precise optometry device according to claim 1, wherein the cylindrical lens pair is selected from a plano-concave/plano-convex cylindrical lens pair, a plano-concave/plano-concave cylindrical lens pair, and a plano-convex/plano-convex cylindrical lens pair, wherein the pair of lens in each lens pair are of the same or different focal power.

6. The subjective and objective integrated precise optometry device according to claim 1, wherein the visual target display device is selected from a CRT display, a commercial projector, a liquid crystal display, a plasma display, an electroluminescent display, an organic light emitting display, a projection display device, and a printed visual chart.

7. The subjective and objective integrated precise optometry device according to claim 1, wherein the first relay telescope is an internal focusing device comprising a first reflector, a first lens, a second reflector, a third reflector, a second lens, and a fourth reflector.

8. An optometry method based on the subjective and objective integrated precise optometry device according to claim 7, comprising:
S1: emitting light from the near-infrared beacon light source, which is collimated by the collimating objective, and then reflected by the second spectroscope and the first spectroscope, and finally enters a human eye through the cylindrical lens pair, and the first relay telescope;
S2: the light reflected from the fundus of the human eye enters the wavefront sensor through the pupil imaging device, the first relay telescope, the cylindrical lens pair, the first spectroscope, and the second relay telescope, so as to objectively measure the refractive error of the human eye;
S3: according to the measured refractive error of the human eye, changing the distance between the two lenses of the first relay telescope along an optical axis to compensate for the human eye defocus based on the human eye defocus correction formula; and according to the measured refractive error of the human eye, cylindrical lenses in the cylindrical lens pair are respectively revolved around an optical axis to compensate for the human eye astigmatism according to the human eye astigmatism correction formula;
S4: upon the compensation for the refractive error of the human eye, displaying a specific visual target on the visual target display device, the human eye observes and judges the specific visual target displayed on the visual target display device through the first relay telescope, the cylindrical lens pair, the first spectroscope, the second spectroscope, the reflector, and the visual target lens;
S5: adjusting the defocus according to the subjective visual perception, the relative angle of the cylindrical lens pair is rotated to adjust and synthesize the magnitude and axial direction of astigmatism till the subjective optimal visual correction quality is obtained, thus finishing the subjective optometry for a single eye; and
S6: upon the subjective optometry for the left and right eyes, moving the left optical path and the right optical path integrally in a vertical direction of optical axis to adjust the pupil distance for red and green and binocular adjustment process, so as to to provide a final binocular refraction correction prescription.

9. An optometry method based on the subjective and objective integrated precise optometry device according to claim 7, comprising:
S1: emitting light from the near-infrared beacon light source, which is collimated by the collimating objective, and then reflected by the second spectroscope and the first spectroscope, and finally enters a human eye through the cylindrical lens pair, and the first relay telescope;
S2: the light reflected from the fundus of the human eye enters the wavefront sensor through the pupil imaging device, the first relay telescope, the cylindrical lens pair, the first spectroscope, and the second relay telescope, so as to objectively measure the refractive error of the human eye;
S3: according to the measured refractive error of the human eye, changing the distance between the two lenses of the first relay telescope along an optical axis to compensate for the human eye defocus based on the human eye defocus correction formula; and according to the measured refractive error of the human eye, cylindrical lenses in the cylindrical lens pair are respectively revolved around an optical axis to compensate for the human eye astigmatism according to the human eye astigmatism correction formula;
S4: upon the compensation for the refractive error of the human eye, displaying a specific visual target on the visual target display device, the human eye observes and judges the specific visual target displayed on the visual target display device through the first relay telescope, the cylindrical lens pair, the first spectroscope, the second spectroscope, the reflector, and the visual target lens; and
S5: providing a diagnosis result according to the judgment of a person under examination, when the person under examination makes a correct judgement, determining that an eye under examination suffers from ametropia and an ametropia measurement value is given, and when the person under examination misjudges, determining that the eye under examination has one or more eye diseases in addition to ametropia.

\* \* \* \* \*